(12) United States Patent
Filimonov et al.

(10) Patent No.: US 12,311,959 B2
(45) Date of Patent: May 27, 2025

(54) SYSTEM AND METHOD FOR DETERMINING COGNITIVE DEMAND

(71) Applicant: Harman Becker Automotive Systems GmbH, Karlsbad-Ittersbach (DE)

(72) Inventors: Andrey Viktorovich Filimonov, Bogorodskiy rayon (RU); Anastasiya Sergeevna Filatova, Nizhegorodskaya oblast (RU); Evgeny Pavlovich Burashnikov, Nizhegorodskaya oblast (RU); Sergey Valeryevich Shishanov, Nizhny Novgorod (RU); Valeriya Alekseevna Demareva, Nizhny Novgorod (RU); Ivan Sergeevich Shishalov, Nizhegorodskaya oblast (RU); Anton Sergeevich Devyatkin, Nizhny Novgorod (RU); Mikhail Sergeevich Sotnikov, Nizhny Novgorod (RU); Anzhela Grigorevna Burova, Nizhny Novgorod (RU); Vladimir Vladimirovich Kilyazov, Nizhegorodskaya Oblast (RU); Anastasiya Vladimirovna Bakhchina, Nizhegorodskaya oblast (RU)

(73) Assignee: HARMAN BECKER AUTOMOTIVE SYSTEMS GMBH, Karlsbad (DE)

( * ) Notice: Subject to any disclaimer, the term of this patent is extended or adjusted under 35 U.S.C. 154(b) by 72 days.

(21) Appl. No.: 18/044,882

(22) PCT Filed: Sep. 11, 2020

(86) PCT No.: PCT/RU2020/000478
§ 371 (c)(1),
(2) Date: Mar. 10, 2023

(87) PCT Pub. No.: WO2022/055383
PCT Pub. Date: Mar. 17, 2022

(65) Prior Publication Data
US 2023/0339479 A1 Oct. 26, 2023

(51) Int. Cl.
*B60W 50/00* (2006.01)
*B60W 40/08* (2012.01)
(Continued)

(52) U.S. Cl.
CPC ........ *B60W 50/0098* (2013.01); *B60W 40/08* (2013.01); *G06V 10/82* (2022.01);
(Continued)

(58) Field of Classification Search
CPC ...... G06V 10/82; G06V 20/597; G06V 40/18; B60W 40/08; B60W 2540/225;
(Continued)

(56) References Cited

U.S. PATENT DOCUMENTS 6,090,051 A 7/2000 Marshall
6,102,870 A 8/2000 Edwards
(Continued)

FOREIGN PATENT DOCUMENTS

CN 109572550 A 4/2019
DE 102015200775 A1 * 7/2016
(Continued)

OTHER PUBLICATIONS

Machine Translation of German Publication No. DE 102015200775 A1 of Decke et al., Jul. 21, 2016, Translated on Sep. 30, 2024.*
(Continued)

*Primary Examiner* — Sisay Yacob
(74) *Attorney, Agent, or Firm* — McCoy Russell LLP

(57) ABSTRACT

System and computer-implemented method for determining a cognitive demand level of a user, the method comprising: recording, as a first training data subset, one or more first
(Continued)

biosignals of a user, wherein the user is occupied with at least one first task, training an artificial neural network on a training dataset to determine a cognitive demand level indicative of cognitive demand the user is experiencing; recording one or more second biosignals of a user of a vehicle as an input dataset; and processing the input dataset by the trained artificial neural network to determine the cognitive demand level indicative of cognitive demand the user is experiencing.

18 Claims, 4 Drawing Sheets

(51) Int. Cl.
| | | |
|---|---|---|
| G06V 10/82 | (2022.01) | |
| G06V 20/59 | (2022.01) | |
| G06V 40/18 | (2022.01) | |

(52) U.S. Cl.
CPC ............ *G06V 20/597* (2022.01); *G06V 40/18* (2022.01); *B60W 2420/403* (2013.01); *B60W 2540/22* (2013.01); *B60W 2540/221* (2020.02); *B60W 2540/225* (2020.02)

(58) Field of Classification Search
CPC ..... B60W 2540/221; B60W 2420/403; B60W 2540/22; B60W 50/0098; A61B 5/02405; A61B 5/163; A61B 5/0077; A61B 5/1103; A61B 5/1128; A61B 5/168; A61B 5/18; A61B 5/6893; A61B 5/7267
See application file for complete search history.

(56) References Cited

U.S. PATENT DOCUMENTS

| | | | |
|---|---|---|---|
| 7,344,251 B2 | 3/2008 | Marshall | |
| 7,435,227 B2 | 10/2008 | Farbos | |
| 7,438,418 B2 | 10/2008 | Marshall | |
| 7,938,785 B2 | 5/2011 | Aguilar et al. | |
| 9,132,839 B1 | 9/2015 | Tan | |
| 9,248,819 B1 | 2/2016 | Tan | |
| 9,646,046 B2 | 5/2017 | Sadowsky et al. | |
| 9,723,992 B2 | 8/2017 | Senechal et al. | |
| 9,763,573 B2 | 9/2017 | Distasi et al. | |
| 9,934,425 B2 | 4/2018 | el Kaliouby et al. | |
| 10,111,611 B2 | 10/2018 | el Kaliouby et al. | |
| 10,368,741 B2 | 8/2019 | Courtemanche et al. | |
| 10,399,575 B2 | 9/2019 | Spasojevic et al. | |
| 2005/0128092 A1* | 6/2005 | Bukman ............... | B60W 40/08 340/576 |
| 2007/0066916 A1 | 3/2007 | Lemos | |
| 2008/0150734 A1 | 6/2008 | Johns | |
| 2010/0117814 A1* | 5/2010 | Lermer ................. | G08B 21/06 340/439 |
| 2018/0125356 A1 | 5/2018 | Yamada | |
| 2018/0125405 A1 | 5/2018 | Yamada | |
| 2018/0125406 A1 | 5/2018 | Yamada | |
| 2019/0038204 A1 | 2/2019 | Beck et al. | |
| 2019/0101985 A1 | 4/2019 | Sajda et al. | |
| 2020/0003570 A1 | 1/2020 | Marti et al. | |
| 2020/0156654 A1 | 5/2020 | Boss et al. | |
| 2021/0245766 A1* | 8/2021 | Sato ....................... | G07C 5/085 |

FOREIGN PATENT DOCUMENTS

| | | |
|---|---|---|
| WO | 2006024129 A1 | 3/2006 |
| WO | 2008107832 A1 | 9/2008 |
| WO | 2015116832 A1 | 8/2015 |

OTHER PUBLICATIONS

Hone, K. et al., "Towards a tool for the Subjective Assessment of Speech System Interfaces (SASSI)," Natural Language Engineering, vol. 6, No. 3-4, Sep. 1, 2000, 17 pages.
"Driver Workload Metrics Project Task 2 Final Report," NHTSA Website, Available Online at https://www.nhtsa.gov/sites/nhtsa.gov/files/documents/driver_workload_metrics_final_report.pdf, Nov. 2006, 460 pages.
Niculescu, A. et al., "Stress and Cognitive Load in Multimodal Conversational Interactions," ResearchGate Website, Available Online at 228782716_Stress_and_Cognitive_Load_in_Multimodal_Conversational_Interactions, May 2010, 6 pages.
Ekanayake, H. et al., "Comparing Expert Driving Behavior in Real World and Simulator Contexts," International Journal of Computer Games Technology, vol. 2013, No. 891431, Aug. 18, 2013, 15 pages.
Barua, S. et al., "Supervised Machine Learning Algorithms to Diagnose Stress for Vehicle Drivers Based on Physiological Sensor Signals," Studies in Health Technology and Infomatics, vol. 211, Jun. 2015, 8 pages.
Deniaud, C. et al., "The concept of "presence" as a measure of ecological validity in driving simulators," Journal of Interaction Science, vol. 3, No. 1, Jul. 13, 2015, 13 pages.
"Energizing comfort control: Wellness while driving," Wayback Machine Internet Archive Website, Daimler Media, Available Online at https://web.archive.org/web/20171031020835/https://media.daimler.com/marsmediasite/en/instance/ko/energizing-comfort-control-wellness-while-driving.xhtml?oid=22934464, Available as Early as Oct. 31, 2017, 4 pages.
McWilliams, T. et al., "Assessing Driving Simulator Validity: A Comparison of Multi-Modal Smartphone Interactions across Simulated and Field Environments," Transportation Research Record: Journal of the Transportation Research Board, vol. 2672, No. 37, Dec. 2018, 8 pages.
"European New Car Assessment Programme (Euro NCAP)," Euro NCAP Website, Available Online at https://cdn.euroncap.com/media/43373/euro-ncap-assessment-protocol-sa-v901.pdf, Feb. 2019, 35 pages.
"Energizing comfort control: Your personal coach is always on board," Mercedes-Benz Group Media Website, Available Online at https://group-media.mercedes-benz.com/marsMediaSite/en/instance/ko/ENERGIZING-comfort-control-Your-personal-coach-is-always-on-board.xhtml?oid=43504472, Jun. 8, 2019, 4 pages.
Chua, S. et al., "Virtual Reality for Screening of Cognitive Function in Older Persons: Comparative Study," Journal of Medical Internet Research, vol. 21, No. 8, Aug. 1, 2019, 10 pages.
Musabini, A. et al., "Heatmap-Based Method for Estimating Drivers' Cognitive Distraction," ArXiv Cornell University Website, Available Online at https://arxiv.org/abs/2005.14136, Available as Early as May 28, 2020, Revised Oct. 31, 2020, 8 pages.
ISA European Patent Office, International Search Report and Written Opinion Issued in Application No. PCT/RU2020/000478, May 11, 2021, WIPO, 30 pages.
State Intellectual Property Office of the People's Republic of China, Office Action and Search Report Issued in Application No. 202080103866.9, Mar. 27, 2025, 25 pages. (Submitted with Partial Translation).

\* cited by examiner

SYSTEM AND METHOD FOR DETERMINING COGNITIVE DEMAND

CROSS-REFERENCE TO RELATED APPLICATIONS

The present application is a U.S. National Phase of International Patent Application Serial No. PCT/RU2020/000478 entitled "SYSTEM AND METHOD FOR DETERMINING COGNITIVE DEMAND," filed on Sep. 11, 2020. The entire contents of each of the above-referenced applications are hereby incorporated by reference for all purposes.

FIELD

The present disclosure relates to systems and methods for determining cognitive demand, and more particularly, to determining the cognitive demand of a driver of a vehicle.

BACKGROUND

Vehicle drivers may be distracted from driving by simultaneously executing one or more additional tasks, or by experiencing stress induced by the traffic situation. This increases the cognitive demand of the driver, which may adversely affect the driver's performance, depending on whether he is distracted or not. Advanced driver assistance systems to support the driver are typically configured for a constant and low cognitive demand. These systems therefore benefit from detecting the cognitive demand of a driver. Accordingly, a need exists for detecting the cognitive demand of a person, in particular of a driver of a car.

The topic of cognitive demand is discussed in:
Niculescu et al., "Stress and Cognitive Load in Multimodal Conversational Interactions", 13th International Conference on Human-Computer Interaction, 19-24 Jul. 2009, San Diego. pp. 891-895
Hone et al., Natural Language Engineering 6, 287 (2000). DOI: 10.1017/S1351324900002497

The validity of driving simulators is disclosed in:
McWilliams, T. et al., Transportation Research Record, 2672, 164 (2018). DOI: 10.1177/0361198118798729.
Deniaud et al., J. Interact. Sci. 3, 1 (2015). DOI: 10.1186/s40166-015-0005-z Ekanayake et al., International Journal of Computer Games Technology 2013, 891431 (2013). DOI:10.1155/2013/891431
Chua et al., J. Med. Internet Res. 21, e14821 (2019), DOI: 10.2196/14821
https://cdn.euroncap.com/media/43373/euro-ncap-assessment-protocol-sa-v901.pdf describes major applications for driver state detection.

The following documents relate to configuring vehicle-mounted electronics according to the state of mind of the driver:
https://media.daimler.com/marsmediasite/en/instance/ko/energizing-comfort-control-wellness-while-driving.xhtml?oid=22934464
https://media.daimler.com/marsmediasite/en/instance/ko/energizing-comfort-control-your-personal-coach-is-always-on-board.xhtml?oid=43504472
https://www.bmwblog.com/2019/11/09/video-how-to-create-a-feel-good-atmosphere-inside-your-new-bmw/
U.S. Pat. No. 9,248,819 B1 and U.S. Pat. No. 9,132,839 B1 disclose methods for customizing a vehicle component control system of a vehicle.
http://www.nhtsa.gov.edgesuite-staging.net/dot/nhtsa/nrd/multimedia/pdfs/crash %20avoidance/driver %20distraction/driver % 20workload %20metrics %20final %20report.pdf discusses the impact of cognitive load on the quality of driving and the driver's performance of driver-related tasks.
European new car assessment programme, Euro NCAP, Assessment Protocol-Safety Assist, Version 9.0.1, February 2019 (https://cdn.euroncap.com/media/43373/euro-ncap-assessment-protocol-sa-v901.pdf.) relates to the problem of determining whether the driver is distracted from driving.

The following disclosures relate to analysis of the state of mind:
U.S. Pat. No. 9,934,425 B2
US 2018/0125405 A1
US 2018/0125356 A1
U.S. Pat. No. 7,344,251 B2
U.S. Pat. No. 6,090,051 A
US 2018/0125406 A1
U.S. Pat. No. 7,435,227 B2
U.S. Pat. No. 7,938,785 B2
WO 2006/024129 A1
U.S. Pat. No. 9,723,992 B2
U.S. Pat. No. 9,646,046 B2
U.S. Ser. No. 10/111,611 B2
U.S. Pat. No. 9,763,573 B2
WO 2015/116832 A1
U.S. Pat. No. 7,438,418 B2
US 2007/0066916 A1
WO 2008/107832 A1
U.S. Pat. No. 6,102,870 A
US 2008/0150734 A1
U.S. Ser. No. 10/399,575 B2 discloses a cognitive load driving assistant.
U.S. Ser. No. 10/368,741 B2 discloses a system for and a method of processing signals sensed from a user.
US 2020/0003570 A1 discloses a system for controlling an autonomous vehicle based on passenger behavior.
US 2020/0156654 A1 discloses a computer-implemented method for operator assessment.
US 2019/0101985 A1 discloses systems and methods for deep reinforcement learning using a brain-artificial intelligence interface.
DE 10 2015/200775 A1 discloses a device, a driver assistance system, a vehicle, and a method for independent assessment of the emotional state and a cognitive load of a driver of a vehicle.

SUMMARY

Disclosed and claimed herein are methods and systems for determining cognitive demand.

The present disclosure relates to a computer-implemented method for determining a cognitive demand of a user. The method comprises
  recording, as a first training data subset, one or more first biosignals of a user, wherein the first biosignals indicate that the user is occupied with at least one first task;
  obtaining, as a second training data subset, information indicative of a cognitive demand that the user is experiencing;

supplying the first training data subset and the second training data subset to an artificial neural network as a training dataset;

training the artificial neural network on the training dataset to determine a cognitive demand level indicative of cognitive demand the user is experiencing;

recording one or more second biosignals of a user of a vehicle as an input dataset; and processing the input dataset by the trained artificial neural network to determine the a cognitive demand level indicative of cognitive demand the user is experiencing.

The disclosure is based on the principle that cognitive demand of a user can be determined using externally observable biosignals. Biosignals are recorded, and a change in biosignals is detected, i. e. a deviation from a baseline. An artificial neural network is trained to determine how the cognitive demand biases biosignals. The artificial neural network may then obtain information on the cognitive demand level, even in a noisy environment such as a vehicle. The term "cognitive demand" is understood to encompass both cognitive load and stress. Cognitive load is related to whether the user is only occupied with the first task, e. g. driving a vehicle, or flying a plane, or whether the user is simultaneously occupied with at least one task in addition to the first task. Stress may be induced by the first task itself. For example, a driver of a vehicle may be stressed by a dangerous traffic situation, or by any other stress-inducing event.

The method comprises a training phase and an inference phase. In the training phase, biosignals are recorded from a subject in a training setting similar to the setting in which the method is to be used. This may be, e. g., a laboratory setup such as a driving simulator or a more realistic situation such as driving a vehicle. Information on the cognitive demand the subject experiencing, in particular if the cognitive demand is increased with respect to the typical cognitive demand of driving, is supplied along with the biosignals as a training dataset to the artificial neural network. The artificial neural network is configured to receive one or more biosignals, such a heart interbeat interval (IBI), or eye gaze, as an input, and to produce an output signal indicative of the cognitive demand level. By training, weights in the artificial neural network are determined that relate the biosignals to the output cognitive demand level signal. In the inference phase, the artificial neural network yields an output signal indicating a cognitive demand level. When the signal exceeds a predetermined threshold, the cognitive demand level is considered high. In response to that determination an output signal is generated, and other connected devices may be configured differently. For example, the sensitivity of a steering wheel or a braking pedal may be modified. Determining the biosignals may include recording data by a sensor and converting the data into a biosignal, by one or more pre-analysis steps as described below.

In an embodiment, the method further comprises converting the one ore more biosignals, after recording the biosignals, into a continuous format indicative of a frequency and/or duration of events per time by applying a time window to the recorded biosignals, the time window in particular being a sliding time window. This preprocessing step allows specifying the biosignal in a useful format, e. g., the number of heart beats by time. By averaging the biosignals over a time window, quick changes are smoothed out. Thereby, if a measurement fails for a short period in time due to noise, a valid signal is continuously available.

In an embodiment, the at least one first task comprises driving a vehicle. The method is particularly useful for determining a driver's cognitive demand level because the driver's biosignal can be obtained with a variety of sensors comprised in the vehicle. Furthermore, determining a driver's cognitive demand level is particularly important to improve road safety.

In an embodiment, the one or more biosignals comprise a heart interbeat interval, IBI. The heart IBI is a particularly useful biosignal as it is related to both cognitive load and stress, and because it can be detected with a plurality of methods including contactless methods.

In an embodiment, recording a biosignal comprises determining the heart interbeat intervals by means of a contact sensor attached to the user. Alternatively, recording the biosignal comprises determining the heart interbeat intervals by means of an RGB camera facing the user. This allows detecting a heart interbeat interval without the need of a sensor that is in direct contact with the user. Thereby, the user can use the system without the need to be connected to a sensor.

In an embodiment, the biosignal comprises eye metrics, in particular one or more of eye gaze, eye openness, and eye movement data. Eye metrics are highly related to cognitive load.

In an embodiment, recording the biosignal comprises: capturing, by a camera, images of the user, and analyzing the images to determine the eye metrics, in particular one or more of eye gaze, eye openness, and eye movement data. This method is contactless and requires only the use of a camera facing the user. This improves the ease of use, in particular in a vehicle.

In an embodiment, the method further comprises analyzing, by a pre-processor, the eye metrics to determine occurrences of one or more of fixation, saccade, and eye blinking, in particular blink duration, eyelid close speed, eyelid open speed. Thereby, entropy in the data is reduced, and the biosignals comprise information particularly adapted for training a neural network.

In an embodiment, the cognitive demand comprises cognitive load related to the user being occupied with at least a second task other than the first task in addition to the first task. This is one of the major applications of the present disclosure. A user, e. g. a driver of a vehicle or a pilot of an aircraft, may be distracted by a plurality of other activities, for example the use of electronic devices, such as a telephone, or by other persons in the vehicle. If the user is occupied by a second task, this induces an increased cognitive load. The cognitive load can then be detected by a biosignal, in particular eye movement characteristics, which are particularly affected by cognitive load. However, other biosignals may as well be used, for example the heart beat interval.

In an embodiment, the method further comprises:
determining that the user is experiencing high cognitive demand, if the determined cognitive load level exceeds a predefined threshold value; and
determining that the user is not experiencing high cognitive demand, if the determined cognitive load level is equal to or below the predefined threshold value.

Thereby, the output of the artificial neural network is transformed into a binary output signal that represents information whether the user is experiencing high cognitive demand or not. In particular, "high cognitive demand" may be defined as a Boolean variable indicative of whether the cognitive demand significantly exceeds the cognitive demand typical for a driving situation. This may be the case either due to the driver being distracted by a second task, or due to stress experienced by the driver. The binary output signal may then be used to control devices and systems comprised in, attached to, or connected to the vehicle.

In an embodiment, the cognitive demand comprises stress. The stress can be sensed by biosignals. For example, a heart interbeat interval is strongly related to stress and therefore well suited for stress detection.

In an embodiment, the method further comprises:
determining that the user is experiencing high cognitive demand, if the determined cognitive demand level exceeds a predefined threshold value within a predetermined period;
and determining that the user is not experiencing high cognitive demand, if the determined cognitive demand level is equal to or below the predefined threshold value within the predetermined period.

Thereby, a binary signal is generated that does not only depend on the current cognitive demand level as determined on-line, but allows also to reacting to a short-time peak in cognitive demand in a predetermined time period in the past. If, for example, the user was stressed due to a stressful traffic situation, there is an increased probability that further stress is imminent, and psychological effects of stress may remain longer than physical effects. Therefore, there is an advantage if the stress level indicated at the output is maintained high for a certain previously determined duration.

In an embodiment, the method further comprises undertaking, based on the determination that the user is experiencing high cognitive demand, one or more of the following actions:
transmission of a warning to one or more vehicles in proximity of the vehicle,
output of a signal to a driver assistance system,
activation of a speed limiter,
adjustment of a sensitivity of a braking pedal or steering wheel,
activation of a lane keeping system,
execution of an automatic emergency stop maneuver,
modification of settings pertaining to an audio, lighting, navigation, and/or air conditioning system in or attached to the vehicle.

These actions have the effect of increasing the traffic safety by reacting to the increased cognitive demand of the driver. Any of these actions may be executed if high cognitive demand is determined in any way as described in the present disclosure. In particular, different actions may be executed depending on whether the cognitive demand is related to cognitive load, i. e. the driver executing a second task, or to a stress level.

In a second aspect of the disclosure, a system for determining a cognitive demand level of a user is provided. The system comprises a first computing device, a first sensor, a second computing device, and a second sensor. The system is configured to execute the steps described above. All properties of the computer-implemented method of the present disclosure are also valid for the system.

BRIEF DESCRIPTION OF THE DRAWINGS

The features, objects, and advantages of the present disclosure will become more apparent from the detailed description set forth below when taken in conjunction with the drawings in which like reference numerals refer to similar elements.

DETAILED DESCRIPTION OF THE PREFERRED EMBODIMENTS

Figure 1:
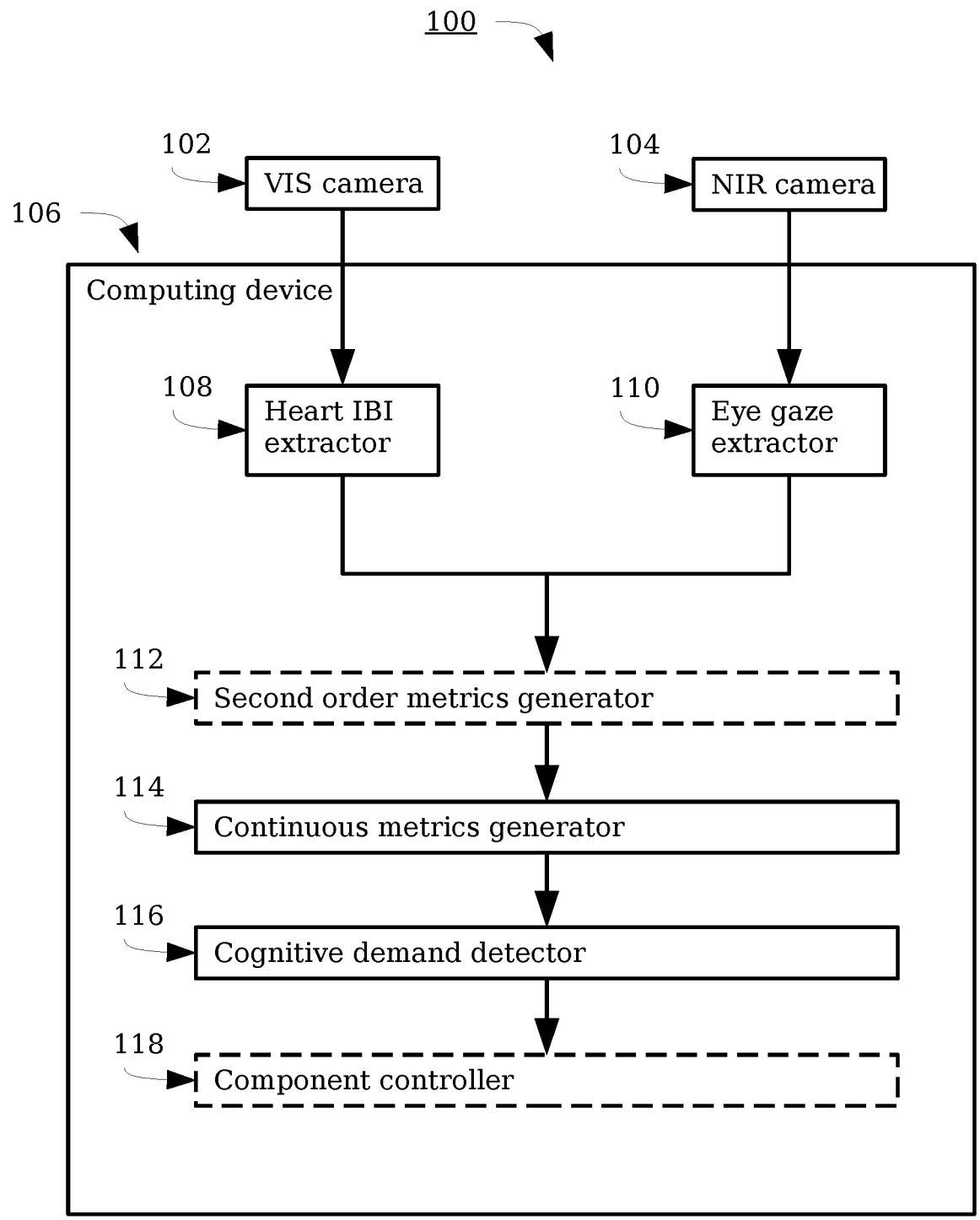
FIG. 1 depicts a block diagram of a system for detecting a cognitive demand level.

FIG. 1 depicts a block diagram of a system 100 for detecting a cognitive demand level. The system comprises a color camera 102 for visible light, and an infrared camera 104. Both cameras face the user of the system, and record images of the user's face. Typical frame rates for the cameras may be, e. g., between 30 frames per second (fps) and 60 fps. The camera resolutions for the infrared camera are high enough to allow determination of eye openness, eye gaze and eye movement. A typical value may be 1280 px×800 px, for example.

The data from the cameras and/or other sensors are processed by a computing device 106. The components 108-118 of the computing device 106 may be implemented in hardware or in software. First, metrics are generated based on the camera images by a metrics generator, which may be implemented as a heart inter-beat interval extractor 108, or an eye gaze extractor 110, to convert the camera image into a biosignal, as discussed with reference to step 206 in FIG. 2 below. The second order metrics generator 112 is an optional component and converts the biosignal into a behavioral pattern with a finite temporal duration and a physiological meaning, as discussed with reference to step 208 in FIG. 2 below. The continuous metrics generator 114 converts the metrics into a continuous form, which may be a plurality of scalar signals that change over time, and that are indicative of the biosignals during a sliding time window, as described with reference to step 210 in FIG. 2 below. The cognitive demand level detector 116 is configured to derive, based on the biosignals, a value indicative of the cognitive demand level. It may be implemented as an artificial neural network, in particular a convolutional neural network. The cognitive demand level detector executes the steps shown in FIG. 3 to determine the cognitive demand level. It is trained by the steps shown in FIG. 4 below. The optional component controller 118 is configured to control or modify settings of other components of the car electronics in response to the cognitive demand level reaching a certain value, in particular if the cognitive demand level is higher than a predefined threshold.

Figure 2:
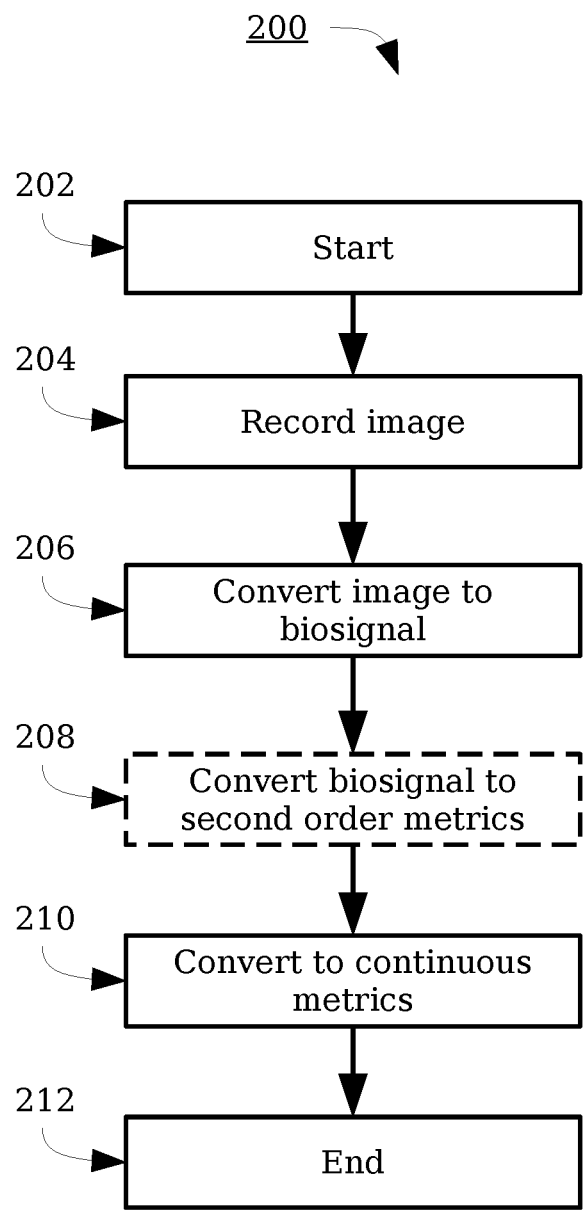
FIG. 2 depicts a flow chart of a method for detecting one or more metrics indicative of cognitive demand level according to an embodiment.

FIG. 2 depicts a flow chart of a method for detecting one or more metrics indicative of a cognitive demand level according to an embodiment.

The process begins, 202, when operation of the system, in particular operation of a vehicle to which the system is attached, is initiated. Images of a user's face are captured with a camera, 204, at a frame rate of 30 fps-60 fps, for example. The following steps are executed for each image, but may comprise re-using intermediate results from previous images. Therefore, the biosignals may be generated at a rate equal to the frame rate of the cameras.

Metrics are generated, 206, based on the camera images. These metrics comprise, in particular, a heart interbeat interval (IBI), and/or eye gaze metrics. To determine a heart IBI, the head of the user is identified on the image and a region of interest is identified that moves with the head if the user turns the head. This generates a signal indicative of the pixel values in the region of interest. After removal of perturbing effects, periodic variations indicative of the heart IBI are found, and the heart IBI is determined based on these periodic variations. This particular process is, however, only an exemplary embodiment of a process for sensing a heart IBI. Alternatively, the heart IBI may be determined by a contact sensor, based on electrocardiography, for example.

In the same step, eye movement characteristics are inferred from the images of the infrared camera 104. On the image, a position of the pupil of a user's eye is determined in relation to the user's head. Thereby, a continuous sequence of coordinates is determined that describes the direction of a vector pointing outwards from the center of the pupil, i. e. normal to the surface of the eye. The coordinates can be either Euler angles or be coordinates of a vector in three-dimensional space. In order to determine by how much the eyes are open, the contours of the upper and lower eyelids are determined, and a maximum distance between them is determined. This maximum distance is an indicator of the openness of the eye and can be normalized, i. e. expressed as a percentage of the state of the eyes being fully open. Alternatively, it can be expressed as a distance in pixels or in millimeters or milliradians using an appropriate calibration. This particular method is, however, only an exemplary embodiment of a sensor for eye gaze and openness information. Furthermore, the present disclosure is not limited to detecting data related to eyes and heart IBI. Other biosignals may be measured in other exemplary embodiments.

Optionally, second order metrics may be derived, 208. This term relates to behavioral patterns with a finite temporal duration, which have a physiological meaning. For example, periods when the eyes are closed (i. e. the openness is below a threshold) may be referred to as blinks. During this time, it is impossible to determine the eye gaze. In contrast, when the eyes are open, the eye gaze can be determined. Fixations are time intervals of slow eye movement, defined as periods during which the eye gaze does not move more than by a two degree angle during a predetermined duration. In contrast, the rest of the time, i. e. when the eyes are moving comparably quickly, is considered a sequence of saccades (periods of fast eye movement). Thereby, any moment in time can be classified unambiguously as belonging to a saccade, a fixation, or a blink. Based on this classification, length of each timeframe, average gaze movement speed, blink duration, eyelid closing speed, eyelid opening speed, and other second order metrics may be determined.

The metrics are further converted into continuous metrics, 210. A heart IBI may be normalized and averaged within a time window. Likewise, blink frequency, eye openness, and eye movement characteristics may be averaged over the duration of a sliding window. In particular, the sliding windows may be of different lengths and shifted with respect to each other. If, for example, high cognitive load leads to a modification in eye movement after a short time and to a different heart IBI after a longer time, the two sliding time windows for these to biosignals that correspond to each other may not be of equal length, and may be non-overlapping.

Furthermore, the discrete sequence of saccades, fixations and blinks may also be transformed into continuous representation. For example, in a predetermined time window of 30 seconds, the user may blink six times, hold three fixations with a total time of 10 seconds and hold four fixations with overall time of 18 seconds. The corresponding continuous metrics comprise then: a number of blinks equal to 6, a number of fixations equal to 3, an overall fixation time equal to 10 seconds, and an average fixation time equal to 3.3 seconds. The window may be sliding so that the next evaluation of continuous metrics may be done within the window starting 1 time unit later, having significant overlap with the previous window. Thereby, the metrics as output signals vary continuously with time, and do not typically jump from one value to an entirely different value from one instant in time to the next. Thereby, the effect of noise and spurious effects on the output signals is reduced. These metrics are then used to determine a cognitive demand level as described with reference to FIG. 3 below, and to train an artificial neural network as described with reference to FIG. 4 below.

Figure 3:
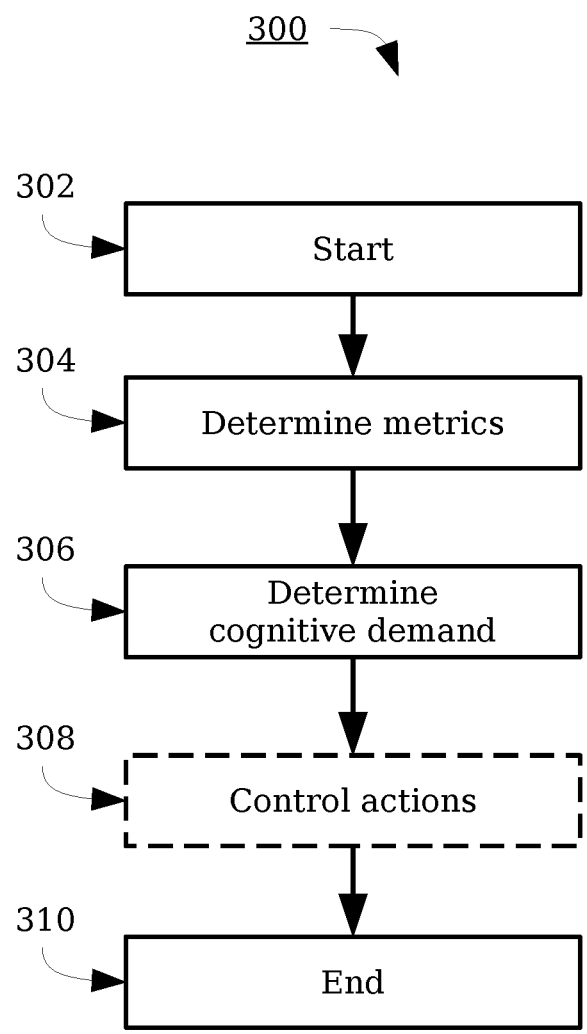
FIG. 3 depicts a flow chart of a method for determining a cognitive demand level according to an embodiment.

FIG. 3 depicts a flow chart of a method for determining a cognitive demand level according to an embodiment.

The process begins, 302, when the operation of the system is initiated. Metrics are determined, 304, according to the process described in FIG. 2. The resulting metrics are used by an artificial neural network to determine the cognitive demand level. The artificial neural network generates a single continuous output value indicative of the cognitive demand level. If the output value exceeds a predetermined threshold, one or more actions are undertaken based on the cognitive demand level, 308.

Controlling or modifying settings may comprise, for example, transmitting a warning to one or more vehicles in proximity of the vehicle to inform them about a stressed or distracted driver. Audio, lighting, navigation, or air conditioning systems in the vehicle may be set to assist the driver focus on traffic. For example, music on the radio may be set to a lower volume. Further, a driver assistance system may be configured differently, e. g. to the effect that the brakes react faster to any action on the braking pedal, or that a lane keeping system is activated. A speed limiter may be activated to prevent the vehicle from exceeding a predetermined maximum speed. Also, an automatic emergency stop maneuver may be executed in case of extreme cognitive demand.

Figure 4:
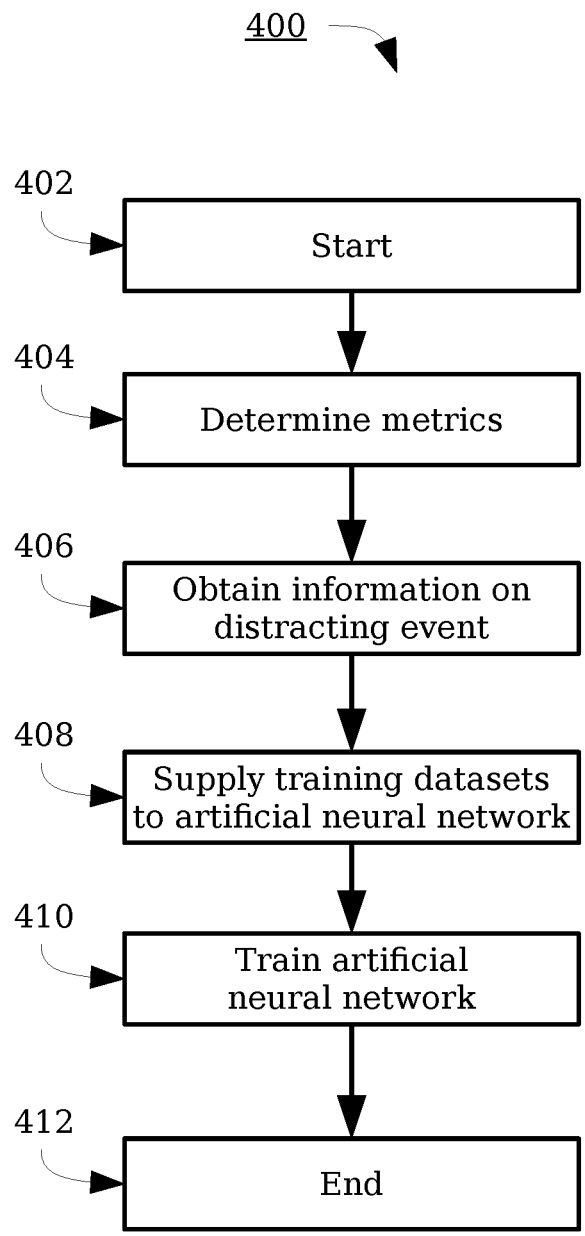
FIG. 4 depicts a flow chart of a method of training of an artificial neural network for determining a cognitive demand level according to an embodiment.

FIG. 4 depicts a flow chart of a method of training of an artificial neural network for determining a cognitive demand level according to an embodiment.

The artificial neural network may be trained by letting a large number of subjects, e. g. some hundred subjects, drive in a car simulator, in a controlled environment. Thereby, the training conditions are more flexible, controllable, and safe. Known driving simulators are sufficiently similar to real-world driving to allow training an artificial neural network.

The biosignals are recorded and processed, 404, in the same way as during execution of the method for inference of the artificial neural network, as described with reference to FIG. 2. The biosignals form the first training data subset. As a controlled variable, the subject may or may not execute a second task in addition to driving at a predetermined time. For example, during a period of ten minutes, the subject only drives the car. For another period of ten minutes, the subject executes an additional task. This variable—whether an additional task is being executed—is entered into the artificial neural network as the second training data subset. The first and second training data subsets are supplied to the artificial neural network as the training dataset, 408. The artificial neural network is trained, 410, on the training dataset.

In an alternative embodiment, the controlled variable is a stress-inducing situation. In order to train the artificial neural network, a potentially dangerous situation occurs and the occurrence is indicated as part of the second training data subset. For example, a simulator may simulate an ordinary traffic situation for ten minutes, and then a series of dangerous situations that also lasts ten minutes. The artificial neural network can be trained using these datasets. This procedure may be improved by measuring the user's stress level using a variety of other methods, such as electrocardiography, or electroencephalography, at the same time, thereby obtaining precise information on the stress level. Additionally or alternatively, the stress level may be characterized by determining correlated values, such as the reaction time of the user, the stability of holding a lane, or time allocation patterns (i. e. how much time the user pays attention to the road, the dashboard, or mirrors, for example). Alternatively or additionally, the expected or realized stress level of the situation may be determined manually after assessment of both situation and recorded data, in order to adjust the second training dataset before initiating training. The second training dataset thus comprises labels given to a period in time upon recording the first training dataset. The labels indicate a stress level according to the assessment based on suitable knowledge from neurophysiological research. This allows training the artificial neural network to detect the stress actually experienced by the user, so that different stress reactions among the training subjects do not induce uncertainty into the training phase. Thus, by reducing the number of false positives and false negatives, the accuracy of the training is improved, i. e. the F1 score is increased. Thereby, a smaller number of training runs is necessary.

EXAMPLES

1. Computer-implemented method for determining a cognitive load level of a user, the method comprising:
    recording, as a first training data subset, one or more first biosignals of a user, wherein the biosignals indicate that the user is occupied with at least one first task;
    obtaining, as a second training data subset, information indicative of whether the user is occupied with at least a second task other than the first task in addition to the first task;
    supplying the first training data subset and the second training data subset to an artificial neural network as a training dataset;
    training the artificial neural network on the training dataset to determine a cognitive load level indicative of whether the user is occupied with at least a second task other than the first task in addition to the first task;
    recording one or more second biosignals of a user as an input dataset; and
    processing the input dataset by the trained artificial neural network to determine the cognitive load level of the user to determine whether the user is occupied with at least a second task other than the first task in addition to the first task.
2. System for determining a cognitive load level of a user, the system comprising:
    a first computing device;
    a first sensor;
    a second computing device (106); and
    a second sensor (102, 104);
    wherein:
        the first sensor is configured to record, as a first training data subset, one or more first biosignals of a user, wherein the biosignals indicate that the user is occupied with at least one first task;
        the first computing device is configured to execute the steps of:
            obtaining, as a second training data subset, information indicative of whether the user is occupied with at least a second task other than the first task in addition to the first task;
            supplying the first training data subset and the second training data subset to an artificial neural network as a training dataset; and
            training the artificial neural network on the training dataset to determine cognitive load level indicative of whether the user is occupied with at least a second task other than the first task in addition to the first task;
        the second sensor (102, 104) is configured to record, as an input dataset, one or more second biosignals of a user; and
        the second computing device (106) is configured to process the input dataset by the trained artificial neural network to determine the cognitive load level of the user to determine whether the user is occupied with at least a second task other than the first task in addition to the first task.
3. Computer-implemented method for determining a stress level of a user, the method comprising:
    recording, as a first training data subset, one or more first biosignals of a user, wherein the biosignals indicate that the user is occupied with at least one first task;
    obtaining, as a second training data subset, information indicative of whether the user is exposed to a stress-inducing situation;
    supplying the first training data subset and the second training data subset to an artificial neural network as a training dataset;
    training the artificial neural network on the training dataset to determine a stress level indicative of whether the user is exposed to a stress-inducing situation;
    recording one or more second biosignals of a user as an input dataset; and
    processing the input dataset by the trained artificial neural network to determine the stress level of the user to determine whether the user is exposed to a stress-inducing situation.
4. System for determining a cognitive load level of a user, the system comprising:
    a first computing device;
    a first sensor;
    a second computing device (106); and
    a second sensor (102, 104);
    wherein:
        the first sensor is configured to record, as a first training data subset, one or more first biosignals of a user, wherein the biosignals indicate that the user is occupied with at least one first task;
        the first computing device is configured to execute the steps of:
            obtaining, as a second training data subset, information indicative of whether the user is exposed to a stress-inducing situation;
            supplying the first training data subset and the second training data subset to an artificial neural network as a training dataset; and training the artificial neural network on the training dataset to determine stress level indicative of whether the user is exposed to a stress-inducing situation;

the second sensor (102, 104) is configured to record, as an input dataset, one or more second biosignals of a user; and the second computing device (106) is configured to process the input dataset by the trained artificial neural network to determine the stress level of the user to determine whether the user is exposed to a stress-inducing situation.

REFERENCE SIGNS

102 RGB camera
104 Infrared camera
106 Computing device
108 Heart inter-beat interval extractor
110 Eye gaze extractor
112 Second order metrics generator
114 Continuous metrics generator
116 Cognitive demand level detector
118 Component controller
200 Method for detecting one or more metrics indicative of a cognitive demand level
202-212 Steps of a method for detecting one or more metrics indicative of a cognitive demand level
300 Method for determining a cognitive demand level
302-310 Steps of a method for determining a cognitive demand level
400 Method of training of an artificial neural network for determining a cognitive demand level
402-412 Steps of a method of training of an artificial neural network for determining a cognitive demand level

The invention claimed is:

1. Computer-implemented method for determining a cognitive demand level of a user, the method comprising:
   recording, as a first training data subset, one or more first biosignals of a user, wherein the first biosignals indicate that the user is occupied with at least one first task;
   obtaining, as a second training data subset, information indicative of a cognitive demand that the user is experiencing;
   supplying the first training data subset and the second training data subset to an artificial neural network as a training dataset;
   training the artificial neural network on the training dataset to determine a cognitive demand level indicative of cognitive demand the user is experiencing;
   recording one or more second biosignals of a user of a vehicle as an input dataset;
   processing the input dataset by the trained artificial neural network to determine the cognitive demand level indicative of cognitive demand the user is experiencing;
   converting the one or more biosignals, after recording the biosignals, into a continuous format indicative of a frequency and/or duration of events per time by applying a time window to the recorded biosignals, the time window being a sliding time window;
   determining that the user is experiencing high cognitive demand, if the determined cognitive demand level exceeds a predefined threshold value within a predetermined period; and
   determining that the user is not experiencing high cognitive demand, if the determined cognitive demand level is equal to or below the predefined threshold value within the predetermined period.

2. The computer-implemented method of claim 1, wherein the at least one first task comprises driving a vehicle.

3. The computer-implemented method of claim 2, wherein the one or more biosignals comprise a heart interbeat interval, IBI.

4. The computer-implemented method of claim 3, wherein recording the biosignal comprises:
   determining the heart interbeat intervals by means of a contact sensor attached to the user; and/or
   determining the heart interbeat intervals by means of an RGB camera facing the user.

5. The computer-implemented method of claim 2, wherein the biosignal comprises eye metrics, including each of eye gaze, eye openness, and eye movement data.

6. The computer-implemented method of claim 5, wherein recording the biosignal comprises:
   capturing, by a camera, images of the user, and
   analyzing the images to determine the eye metrics.

7. The computer-implemented method of claim 5, further comprising:
   analyzing, by a pre-processor, the eye metrics to determine occurrences of one or more of fixation, saccade, and eye blinking.

8. The computer-implemented method of claim 1, wherein the cognitive demand comprises a cognitive load of the user related to the user being occupied with at least a second task other than the first task in addition to the first task.

9. The computer-implemented method of claim 8, further comprising:
   determining that the user is experiencing high cognitive demand, if the determined cognitive demand level exceeds a predefined threshold value; and
   determining that the user is not experiencing high cognitive demand, if the determined cognitive demand level is equal to or below the predefined threshold value.

10. The computer-implemented method of claim 1, wherein the cognitive demand comprises stress.

11. The computer-implemented method of claim 1, further comprising:
    undertaking, based on the determination that the user is experiencing high cognitive demand, the following actions:
    transmission of a warning to one or more vehicles in proximity of the vehicle,
    output of a signal to a driver assistance system,
    activation of a speed limiter,
    adjustment of a sensitivity of a braking pedal or steering wheel, activation of a lane keeping system,
    execution of an automatic emergency stop maneuver, and
    modification of settings pertaining to an audio, lighting, navigation, and/or air conditioning system in or attached to the vehicle.

12. System for determining a cognitive demand level of a user, the system comprising:
    a first computing device;
    a first sensor;
    a second computing device; and
    a second sensor;
    wherein:

the first sensor is configured to record, as a first training data subset, one or more first biosignals of a user, wherein the biosignals indicate that the user is occupied with at least one first task;

the first computing device is configured to execute the steps of:

obtaining, as a second training data subset, information indicative of a cognitive demand that the user is experiencing;

supplying the first training data subset and the second training data subset to an artificial neural network as a training dataset; and training the artificial neural network on the training dataset to determine a cognitive demand level indicative of cognitive demand the user is experiencing;

the second sensor is configured to record, as an input dataset, one or more second biosignals of a user; and the second computing device is configured to process the input dataset by the trained artificial neural network to determine the cognitive demand level indicative of cognitive demand the user is experiencing, wherein the biosignals comprise eye metrics, including each of eye gaze, eye openness, and eye movement data, wherein the eye metrics are analyzed to determine occurrences of one or more of fixation, saccade, and eye blinking, and further wherein the biosignals include second order metrics that are based on a classification of time into one of the following: time belonging to a saccade; time belonging to a fixation; and time belonging to a blink.

13. The system of claim 12,
wherein the first computing device and the second computing device are further configured to:
convert the one or more biosignals, after recording the biosignals, into a continuous format indicative of a frequency and/or duration of events per time, by applying a time window to the recorded biosignals.

14. The system of claim 13,
wherein the at least one first task comprises driving a vehicle.

15. The system of claim 14,
wherein the one or more biosignals comprise a heart interbeat interval, IBI.

16. The system of claim 15,
wherein the first sensor and/or the second sensor comprises an RGB camera, and recording the biosignal comprises:
determining the heart interbeat intervals by means of a contact sensor attached to the user; and/or determining the heart interbeat intervals by means of the RGB camera facing the user.

17. The system of claim 12,
wherein the first sensor and/or the second sensor comprises a camera, and recording the biosignal comprises:
capturing, by the camera, images of the user, and analyzing the images to determine the eye metrics.

18. Computer-implemented method for determining a cognitive demand level of a user, the method comprising:
recording, as a first training data subset, one or more first biosignals of a user, wherein the first biosignals indicate that the user is occupied with at least one first task;

obtaining, as a second training data subset, information indicative of a cognitive demand that the user is experiencing;

supplying the first training data subset and the second training data subset to an artificial neural network as a training dataset;

training the artificial neural network on the training dataset to determine a cognitive demand level indicative of cognitive demand the user is experiencing;

recording one or more second biosignals of a user of a vehicle as an input dataset;

processing the input dataset by the trained artificial neural network to determine the cognitive demand level indicative of cognitive demand the user is experiencing;

converting the one or more biosignals, after recording the biosignals, into a continuous format indicative of a frequency and/or duration of events per time by applying a time window to the recorded biosignals, the time window being a sliding time window;

determining that the user is experiencing high cognitive demand, if the determined cognitive demand level exceeds a predefined threshold value within a predetermined period; and determining that the user is not experiencing high cognitive demand, if the determined cognitive demand level is equal to or below the predefined threshold value within the predetermined period, wherein the one or more biosignals comprise eye metrics, including each of eye gaze, eye openness, and eye movement data, wherein the eye metrics are analyzed to determine occurrences of one or more of fixation, saccade, and eye blinking, and further wherein the biosignals include second order metrics that are based on a classification of time into one of the following: time belonging to a saccade; time belonging to a fixation;

and time belonging to a blink.

* * * * *